US00PP12815P2

(12) United States Plant Patent
Hinkley

(10) Patent No.: US PP12,815 P2
(45) Date of Patent: Jul. 30, 2002

(54) *CAMPANULA TAKESIMANA* PLANT NAMED 'BEAUTIFUL TRUST'

(75) Inventor: Daniel J. Hinkley, Kingston, WA (US)

(73) Assignee: Burphe/Heronswood, Inc., Kingston, WA (US)

( * ) Notice: Subject to any disclaimer, the term of this patent is extended or adjusted under 35 U.S.C. 154(b) by 9 days.

(21) Appl. No.: 09/785,826

(22) Filed: Feb. 16, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—Klarquist Sparkman, LLP

(57) ABSTRACT

A new and distinct cultivated variety of *Campanula takesimana* plant characterized by a unique combination of stellate, white blooms, with ligulate petals, and rhomboidal to elliptical, glossy, green foliage.

1 Drawing Sheet

The present invention relates to a new and distinct cultivated variety of *Campanula takesimana,* of the family Campanulaceae, which originated as a unknown mutation of *Campanula takesimana.* The instant plant was discovered by the applicant in the garden of a friend in S. Korea. The plant was subsequently given to the applicant as a gift.

This new variety has been reproduced only by asexual propagation via division and tissue culture. Each of the progeny exhibits identical characteristics to the original plant.

This plant is characterized by the following:

1. Unique stellate floewr shape unlike any other Campanulas known to the applicant.
2. White flowers.
3. Green, glabrous, glossy, leathery foliage.
4. Unusual rhomboidal to elliptical-shaped foliage unlike the cordate-shaped leaves of the species.

Asexual propagation by division and tissue culture as done in Canby, Oreg., and Kingston, Wash., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows 1.5-year-old plant of *Campanula takesimana* 'Beautiful Trust' in bloom, growing a two-gallon pot, in Camby, Oreg.

DETAILED PLANT DESCRIPTION

The following is a detailed description of the new *Campanula takesimana* variety based on observations of specimens in Canby, Oreg. The color descriptions are all based on The Royal Horticultural Society Colour Chart.

Botanical classification: *Campanula takesimana* 'Beautiful Trust'.

Foliage:

*Type.*—Semi-evergreen (evergreen in USDA Zones 8–9, herbaceous in USDA Zones 5–7).
*Shape.*—Rhomboidal to elliptical with unequal sides.
*Length.*—7–11 cm.
*Width.*—2.5–5.5 cm at widest point.

*Petiole length.*—14–16 cm.
*Margins.*—Incised-toothed.
*Apex.*—Acuminate to narrowly-acute.
*Base.*—Attenuate.
*Leaf texture.*—Glabrous, leathery. Glossy in appearance.
*Petiole texture.*—Glabrous.
*Leaf arrangement.*—Rosette.
*Venation.*—Pinnately-reticulate.

Size of a 2-year-old plant grown in a 2.5-gallon pot in a greenhouse in Canby, Oreg. (data taken in winter):

*Height.*—17 cm.
*Width.*—46 cm.

Flower:

*Type.*—Perfect. Complete.
*Shape.*—Stellate. Individual petals are ligulate or strap-like and may recurve strongly backwards.
*Size.*—Individual petals are 4–5 mm wide by 3.5–5.5 cm long. Whole flower opens to 8 cm across from petal tip to petal tip.
*Sepals.*—to 4 cm long by 1 cm wide, linear to oblanceolate, margins entire to slightly undulate, and glabrous.
*Sepal count.*—5.
*Petal count.*—5.
*Petal texture.*—Outside is glabrous and villous on the inside.
*Ovary position.*—Partly inferior.
*Carpel number.*—3.
*Style length.*—1.7 cm long.

*Stamen number.*—5.

*Anther size.*—4 mm long by 1.5 mm wide when pollen becomes evident.
*Inflorescence type.*—Panicle.
*Flower number per inflorescence.*—30–50.
*Peduncle width.*—3 mm tapering to 1 mm pedicels.
*Peduncle texture.*—Glabrous.
*Blooming height.*—Approximately 74 cm.
*Bloom period.*—June to July in Canby. Oreg.
*Fragrance.*—None.
*Lastingness.*—Individual blooms, on the plant, last up to 7 days from anthesis. Whole inflorescence, on the plant, lasts up to a month. Cut blooms wilt within a day if no special treatment is given. Currently, no treatment has been devised to maintain blooms longer when cut.

Fruit:
*Type.*—3-celled capsule.
*Size.*—5 mm width by 8 mm length.
*Fertility.*—Low.
Seed:
*Size.*—Minute. 1 mm long by 0.5 mm wide.
*Shape.*—Oval.
Habit: Spreading by rhizomes. Moderate-fast growth rate.
Disease: None observed on plants grown commercially in Canby, Oreg.
Hardiness: Cold hardy to USDA Zone 5.

Color Characteristics

Foliage (blade):
*Upper surface.*—RHS 137A to B Green Group.
*Lower surface.*—RHS 137B to C Green Group to RHS 146B or 147B.
Petiole: Ranges from RHS 144B to 145C Yellow-Green Group depending on the light. In lower light conditions it is 145C. In high light conditions it is 144B.
Flower:
*Petal* (*including inside hairs*).—RHS 155C White Group.
*Pistil.*—RHS 155C White Group.
*Sepal.*—RHS 144A to B Yellow-Green Group.
*Pollen anther.*—RHS 199D Grey-Brown Group.
Peduncle: RHS 144A Yellow-Green Group.
Fruit: RHS 144A to B Yellow-Green Group.
Seed: RHS 192B Greyed-Brown Group.

DESCRIPTION OF PARENT PLANTS

The instant plant resulted from an unknown mutation of *Campanula takesimana*. *Campanula takesimana,* as described in *Botanica's Annuals & Perennials* (1999), has "unusually long bell-shaped flowers, satiny creamy white to lilac-pink outside but spotted with darker purple-brown inside. The large leaves form loose basal rosettes, and the roots tend to spread so the plant forms a large clump. The flowering stems are up to 3 ft long but are usually weak and reclining. The cultivar 'Alba' has white flowers." The instant plant differs from *Campanula takesimana* in having star-shaped flowers, with strap-like petals, instead of bell-shaped flowers. The instant plant also differs in having rhomboidal to elliptical-shaped leaves instead of cordate-shaped leaves that are observed on the species.

I claim:

1. A new and distinct cultivated variety of *Campanula takesimana* plant substantially as shown and described, characterized by a unique combination of stellate, white blooms, with ligulate petals, and rhomboidal to elliptical, glossy, green foliage.

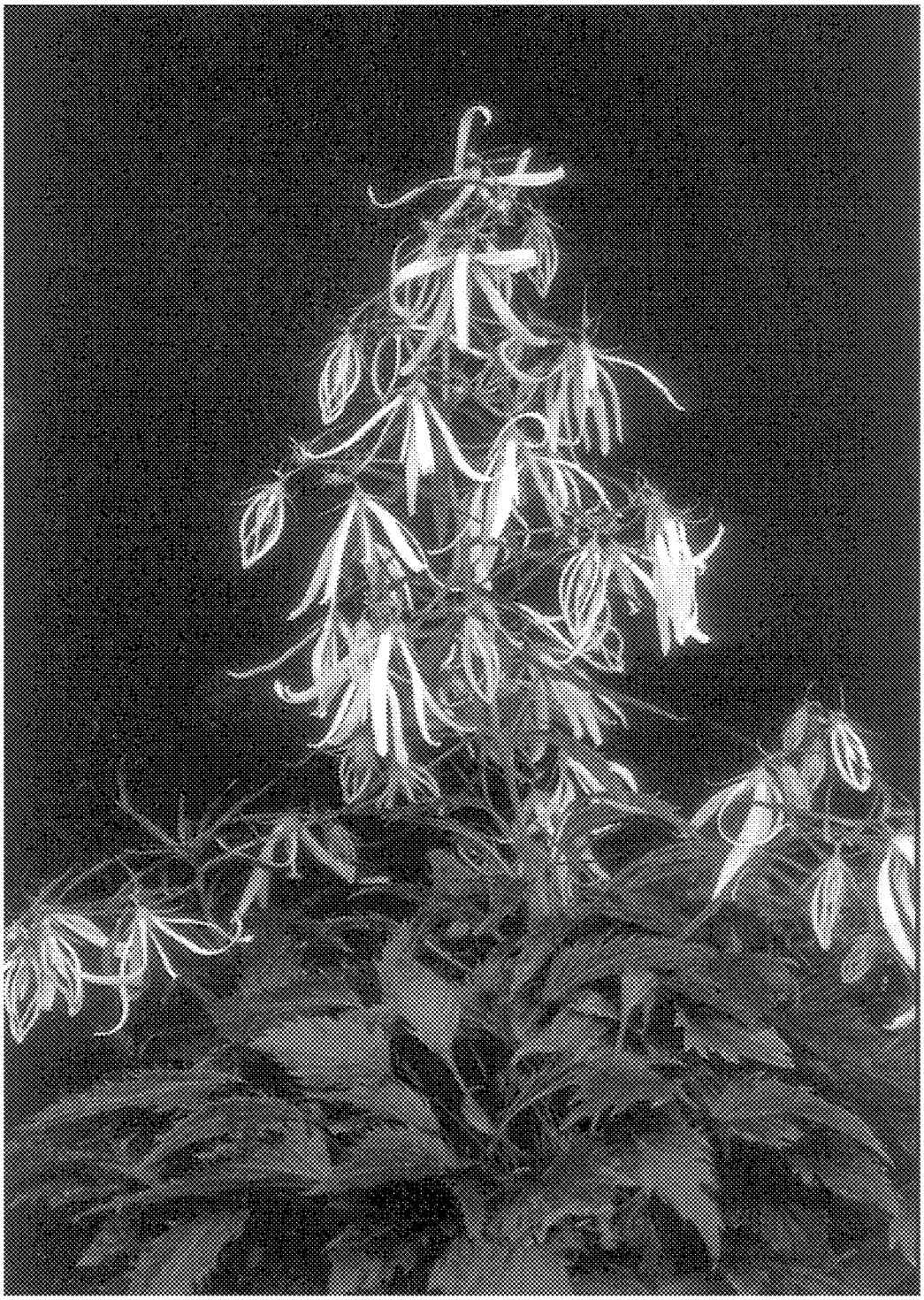

* * * * *